United States Patent [19]
Malavarca et al.

[11] Patent Number: 4,618,408
[45] Date of Patent: Oct. 21, 1986

[54] CASTING APPARATUS FOR ELECTROPHORETIC GEL TRAY

[75] Inventors: Richard Malavarca, South Orange; Thomas Livelli, Lyndhurst, both of N.J.

[73] Assignee: Lab Stuff, Inc., South Orange, N.J.

[21] Appl. No.: 675,984

[22] Filed: Nov. 29, 1984

[51] Int. Cl.$^4$ .................................... G01N 27/28
[52] U.S. Cl. ........................ 204/299 R; 204/182.8; 249/155; 249/160; 249/165; 249/112
[58] Field of Search ............... 249/112, 155, 160, 162, 249/158, 163, 165, 184; 204/180 G, 299 R, 182.8

[56] References Cited

U.S. PATENT DOCUMENTS

| | | | |
|---|---|---|---|
| 824,235 | 6/1906 | Damon | 249/165 |
| 968,285 | 7/1910 | Streator | 249/143 |
| 1,166,770 | 1/1916 | Latham | 62/350 |
| 1,829,114 | 10/1931 | Schroeder | 249/112 |
| 3,635,808 | 1/1972 | Elevitch | 204/299 R |
| 3,762,877 | 10/1973 | Rains et al. | 436/180 |
| 3,766,047 | 10/1973 | Elevitch | 204/299 R |
| 3,767,560 | 10/1973 | Elevitch | 204/299 R |
| 3,785,608 | 1/1974 | Heinzman et al. | 249/163 |
| 3,803,020 | 4/1974 | Stephan | 204/299 R |
| 4,035,377 | 7/1977 | Detroy | 204/299 R |
| 4,194,863 | 3/1980 | Denckla | 204/299 R |
| 4,199,129 | 4/1980 | Fischer | 249/158 |
| 4,234,400 | 11/1980 | Kaplan et al. | 204/299 R |
| 4,314,897 | 2/1982 | Monte et al. | 204/299 R |

FOREIGN PATENT DOCUMENTS 1003047  9/1965  United Kingdom ................ 249/155

OTHER PUBLICATIONS

*BRL Catalog and Reference Guide*, dated 1983, pp. 48-51.
*Chromotography Electrophoresis Immunochemistry and HPLC*, copyrighted 1983, pp. 143-145.
*Hoffer Scientific Instruments*, copyrighted 1983, pp. 26-33.
*International Biotechnologies, Inc., Products for Molecular Biology*, copyrighted 1983, pp. 132-137.

Primary Examiner—John F. Niebling
Assistant Examiner—B. J. Boggs, Jr.
Attorney, Agent, or Firm—Lerner, David, Littenberg, Krumholz & Mentlik

[57] ABSTRACT

A casting apparatus for receiving electrophoretic gel trays is disclosed. The casting apparatus includes a pair of spaced apart seal elements which are movable with respect to one another to provide one or, more openings of varying size to receive a corresponding gel tray therein. The open ends of the gel tray are sealed by the seal elements so that hot argrose or polyacrylamide gel may be poured into the gel tray for forming a gel layer of predetermined thickness. The seal elements are maintained in sealing engagement with the open ends of the gel trays by means of a rod frictionally engaged between a portion of the housing forming the casting apparatus and one of the seal elements.

20 Claims, 4 Drawing Figures

CASTING APPARATUS FOR ELECTROPHORETIC GEL TRAY

BACKGROUND OF THE INVENTION

The present invention relates in general to a casting apparatus for electrophoretic gel trays, and more particularly, to such an apparatus adapted for casting a separation medium such as agarose and polyacrylamide gels in an open ended gel tray for horizontal gel electrophoresis, for example, in DNA separation systems.

Electrophoresis is an analytical method widely used in research and increasingly advantageous for clinical and analytical processes. While there is known a variety of electrophoresis devices and methods, e.g., thin-film and column electrophroesis, the type of electrophoresis with which the present invention is principally concerned is commonly referred to as horizontal gel electrophoresis. In this regard, for many educational, laboratory, medical, research or industrial purposes, gel electrophoresis has been employed to study migration of a substance in a suitable retarding medium and/or to effect separation of complex substances by differential migration in such media. The driving force for inducing the migration is an applied electric field, where the medium is capable of retarding the movement of the substance as a function of its molecular weight, charge and molecular size.

Electrophoresis is carried out in the separation medium which is cast to a predetermined thickness in a gel tray typically having open ends. In order to permit the formation of a gel layer of predetermined thickness, the gel tray is placed into a casting apparatus enclosed on all four sides, so as to overcome the necessity of having to tape up the open ends of the tray in order to pour the gel. As gel trays are used in a variety of sizes, there is the need to inventory a corresponding number of casting apparatus of compatible sizes. In addition, as each casting apparatus can accommodate only one gel tray at a time, multiple trays of the same size cannot be prepared simultaneously with a gel layer for increased efficiency of operation. As both the casting apparatus and gel trays are relatively expensive, the necessity of maintaining a large number of same is undesirable.

The foregoing casting apparatus, although enclosing the gel tray on all four sides, often provides an ineffective seal at the open ends of the tray. As a consequence, hot gel when poured into the gel tray, can leak around the open ends of the tray and under its peripheral edges. Once the hot gel solidifies, it becomes relatively difficult to remove the gel tray from the casting apparatus, as the solidified gel acts as an adhesive. The force necessary to remove the gel tray can result in breakage to the tray or injury to the formed gel layer. Accordingly, it can be appreciated that there is an unsolved need for a casting apparatus which is adapted to accommodate multiple gel trays of the same or different size and one which provides a positive seal at the open ends of the tray while facilitating its removal upon solidification of the gel.

SUMMARY OF THE INVENTION

It is broadlly an object of the present invention to provide a casting apparatus for electrophoretic gel trays specifically adapted for DNA electrophoresis systems which overcome or avoids one or more of the foregoing disadvantages resulting from the use of the above-mentioned prior art casting apparatus/gel tray combination, and which fulfills the specific requirements of such a casting apparatus for horizontal gel electrophoresis. Specifically, it is within the contemplation of one aspect of the present invention to provide a casting apparatus for an electrophoretic gel tray which greatly facilitates the formation of a gel layer of predetermined thickness.

Another object of the present invention is to provide a casting apparatus for an electrophoretic gel tray which is simple and efficient to use in the formation of a gel layer in trays of different size.

Another object of the present invention is to provide a casting apparatus for an electrophoretic gel tray which will accommodate multiple trays of the same or different size for increased efficiency of operation.

Another object of the present invention is to provide a casting apparatus for an electrophoretic gel tray which provides a temporary leak-proof seal for the opening ends of the gel tray.

Another object of the present invention is to provide a casting apparatus for an electrophoretic gel tray which prevents sealing of the gel tray within the casting apparatus by leakage of hot gel around and under the tray.

In accordance with one embodiment of the present invention, there is provided an apparatus for receiving a tray having open ends for casting a medium therein. The apparatus is constructed of a housing, first and second sealing means arranged spaced apart within the housing for sealing the open ends of the tray when brought into engagement therewith, the first sealing means being movable with respect to the second sealing means, and guide means in operative association with the first sealing means for adjusting the spaced apart relationship between the first and second sealing means so as to receive the tray therebetween with the open ends in sealing engagement with the first and second sealing means.

In accordance with another embodiment of the present invention there is provided an apparatus for receiving a tray having open ends for casting a medium therein. The apparatus is constructed of a housing, first and second sealing means arranged opposing one another in spaced apart relationship within the housing for sealing the open ends of the tray when brought into engagement therewith, the first and second sealing means being movable with respect to each other, guide means in operative association with the first and second sealing means for adjusting the spaced apart relationship between the sealing means to provide a first opening for receiving the tray with its open ends in engagement with the first and second sealing means, and securing means for maintaining the first and second sealing means in sealing engagement with the open ends of the tray.

BRIEF DESCRIPTION OF THE DRAWINGS

The above description, as well as further objects, features and advantages of the present invention will be more fully understood by reference to the following detailed description of a presently preferred, but nonetheless illustrative casting apparatus for an electrophoretic gel tray in accordance with the present invention when taken in conjunction with the accompanying drawings wherein.

DETAILED DESCRIPTION

Figure 1:
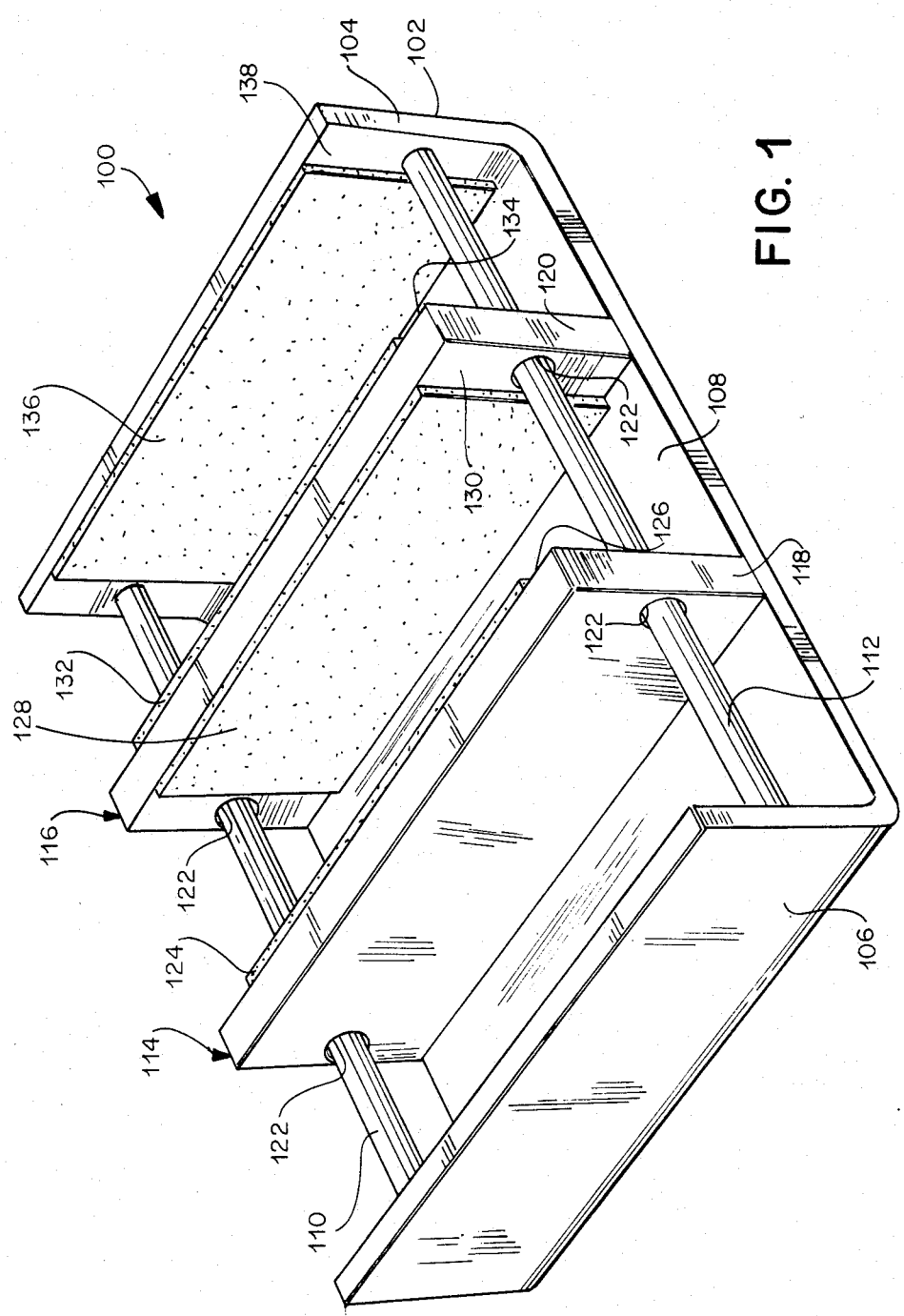
FIG. 1 is a perspective view of the casting apparatus of the present invention showing its construction to include a housing which contains a pair of spaced apart movable seal elements supported on a pair of parallel spaced apart guide rods.

Referring now to the drawings wherein like reference numerals represent like elements, there is shown in FIG. 1 a perspective view of a casting apparatus in accordance with the present invention and generally indicated by reference numeral 100. The casting apparatus 100 permits the formation of a gel layer such as agarose and polyacrylamide gels in an open ended gel tray for horizontal gel electrophoresis. One specific application to which the casting apparatus is uniquely suitable, is in the preparation of a gel layer of predetermined thickness in DNA electrophoresis systems. However, it is to be understood that the casting apparatus 100 of the present invention is suitable for use in gel electrophoresis which is employed to study migration of a substance in a suitable retarding medium and/or to effect separation of complex substances by differential migration in such media.

The casting apparatus 100 is constructed from a U-shaped housing 102 having a pair of spaced apart upstanding side walls 104, 106 separated by a planar base 108. A pair of elongated guide rods 110, 112 are arranged in spaced apart parallel relationship between the side walls 104, 106 overlying the base 108. The guide rods 110, 112 are secured at their terminal ends to the side walls 104, 106 at a predetermined distance above the base 108.

A pair of seal elements 114, 116 are movably positioned between the side walls 104, 106 of the housing 102. Each of the seal elements 114, 116 are constructed of an elongated partition 118, 120 having openings 122 provided at their opposite ends for receiving the guide rods 110, 112. In this manner, the seal elements 114, 116 are movable between the side walls 104, 106 of the housing 102 in parallel relationship with one another. A gasket 124 is provided on the inwardly facing vertical surface 126 of the seal element 114. Likewise, a gasket 128 is provided on the inwardly facing vertical surface 130 of the seal element 116. A gasket 132 is also provided on the outwardly facing vertical surface 134 of the seal element 116. Finally, a gasket 136 is provided on the inner vertical surface 138 of the side wall 104. The gaskets 124, 128, 132, 136 are made of low density polyethelene material, for example, neoprene. Each of the gaskets 124, 128, 132, 136 extend lengthwise between the guide rods 110, 112 and widthwise to a location adjacent the base 108 of the housing 102.

Figure 2:
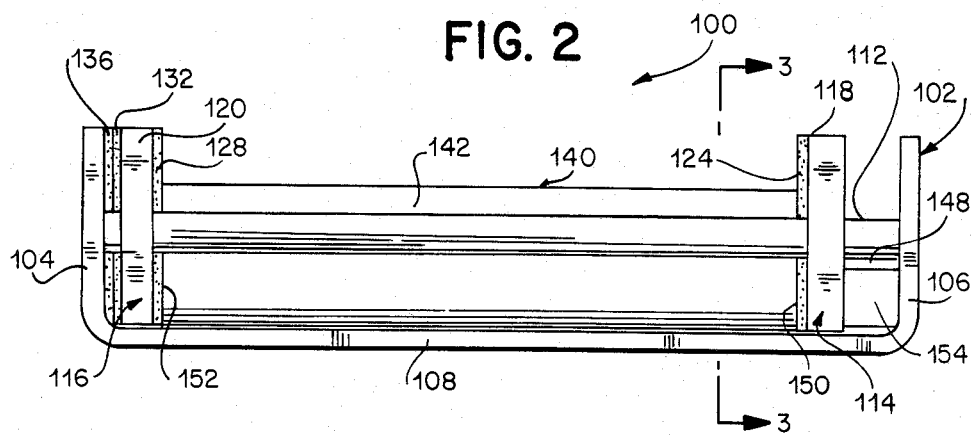
FIG. 2 is a front elevational view showing the seal elements engaging the open ends of a gel tray and secured thereat by a rod arranged between one of the seal elements and a portion of the housing.
Figure 3:
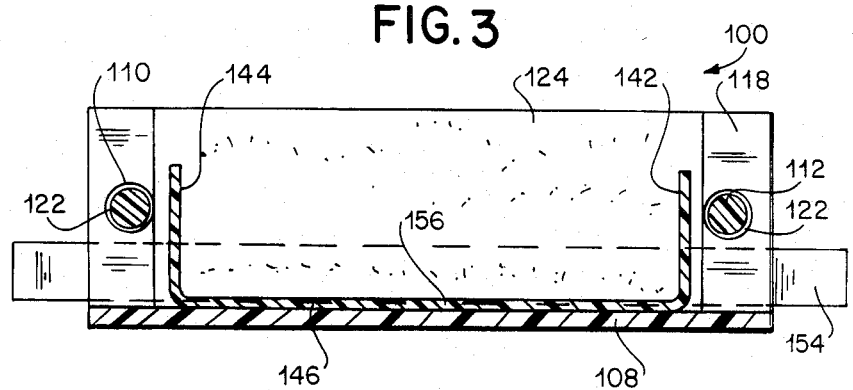
FIG. 3 is a cross-sectional view taken along line 3—3 of FIG. 2 showing one of the seal elements in its cooperative arrangement with the guide rods for movement thereof within the housing.

The use of the casting apparatus 100 for forming a gel layer of predetermined thickness in a single gel tray will be described with reference to FIGS. 2 and 3, while in multiple gel trays in accordance with FIG. 4. Referring now specifically to FIGS. 2 and 3, a U-shaped gel tray 140 is constructed of a pair of upstanding side walls 142, 144 and a connecting base 146. The gel tray 140 is received within a first opening formed between the spaced apart seal elements 114, 116. In order to provide the first opening, seal element 116 is slid along the guide rods 110, 112 until arranged adjacent side wall 104. In this manner, side wall 104 acts as a stop for the seal element 116 by the abutment of the gaskets 132, 136. In a similar manner, the seal element 114 is slid along the guide rods 110, 112 in a direction away from seal element 116 to provide an opening of sufficient size for receiving the gel tray 140 therein. As shown, the seal element 114 is arranged adjacent, but spaced from the side wall 102 to form an opening 148 therebetween.

The base 146 of the gel tray 140 is supported by the base 108 of the casting apparatus 100. The open ends 150, 152 of the gel tray 140, formed by the leading edges of the side walls 142, 144 and base 146, are brought into engagement with the opposing gaskets 124, 128 of the seal elements 114, 116. As a result of the engagement of the gaskets 124, 128 with the open ends 150, 152 of the seal elements 114, 116, a fluid-tight seal is provided thereat.

The fluid-tight seal is maintained by securing the seal elements 114, 116 in their respective positions by means of an elongated rod 154. The rod is dimensioned to be frictionally received within the opening 148 formed between the guide rods 110, 112 and the base 108 of the housing 102. Thus, as the length of the gel tray 140 increases or decreases, the cross-sectional dimension of the rod 154 will change accordingly. In this manner, the rod 154 maintains the gaskets 124, 128 of the seal elements 114, 116 in fluid-tight sealing engagement with the open ends 150, 152 of the gel tray. Hot gel can then be poured into the gel tray 140 to provide a gel layer 156 of predetermined thickness upon solidification. The seal created by the gaskets 124, 128 of the seal elements 114, 116 prevents leakage of hot gel around and under the open ends 150, 152 of the gel tray 140. Once the gel layer 156 has formed, the tray 140 can be removed by first removing rod 154 from within the opening 148 and sliding the seal element 114 along the guide rods 110, 112 towards the side wall 106, so as to increase the opening created between the seal elements 114, 116 and thereby releasing the gel tray.

Figure 4:
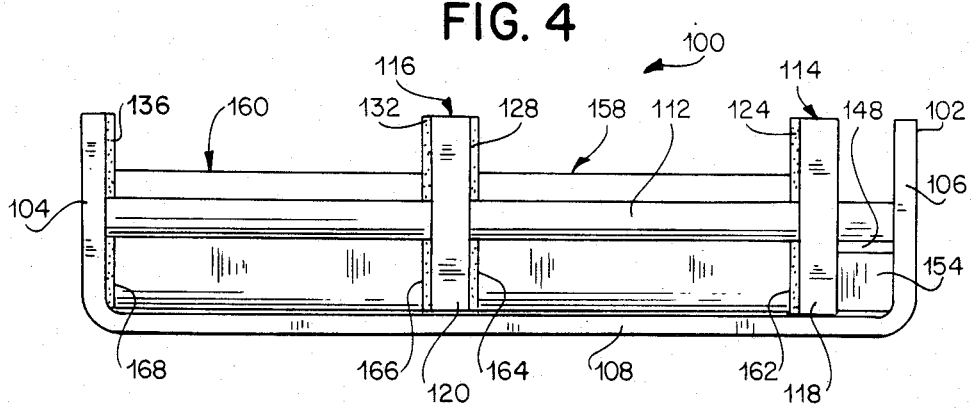
FIG. 4 is a front elevational view of the casting apparatus as shown in FIG. 1 having the seal elements arranged alternatively for receiving a pair of gel trays with their open ends sealed by the seal elements.

Referring now to FIG. 4, the casting apparatus 100 is shown in an arrangement whereby a pair of gel trays 158, 160 of the same or different size, are received within the casting apparatus. Gel tray 158 is received within a first opening formed between the seal elements 114, 116, while the other gel tray 160 is received within an opening formed between seal element 116 and the side wall 104 of the housing 102. In this manner, the open ends 162, 164 of gel tray 158 are sealed by gaskets 124, 128 of the seal elements 114, 116. Similarly, the open ends 166, 168 of the gel tray 160 are sealed by gasket 132 of seal element 116 and gaskey 136 provided on side wall 104 of the housing 102. The opening for receiving gel tray 160 is provided by sliding the seal element 116 along the guide rods 110, 112 away from side wall 104. The gaskets 124, 128, 132 of the seal element 114, 116 and the gasket 136 provided on the side wall 104 are maintained in sealing engagement with the open ends 162, 164, 166, 168 of the gel trays 158, 160 by means of the rod 154 being frictionally received within the opening 148 in the manner described with reference to FIG. 3.

As thus far described, the casting apparatus 100 of the present invention will accommodate single or multiple gel trays of different size to facilitate the formation of a gel layer of predetermined thickness therein. The casting apparatus 100 provides a temporary leak-proof seal for the open ends of the gel tray, simply and quickly, for increased efficiency of operation.

In accordance with the present invention, there has thus far been described an apparatus capable of receiving a plurality of trays having open ends for casting a gel therein. The apparatus is constructed of a housing, first, second and third seal elements arranged within the housing in spaced apart relationship, the first and second seal elements being movable with respect to each other, guide means for adjusting the relative position of the first and second seal elements within the housing for providing (1) a first receiving portion between the first and second seal elements for receiving a first tray therein with its open ends in engagement with the first and second seal elements and (2) a second receiving portion between the second and third seal elements for receiving a second tray therein with its open ends in engagement with the second and third seal elements, and securing means for maintaining the first, second and third seal elements in engagement with the open ends of the first and second trays.

Although the invention herein has been described with reference to particular embodiments, it is to be understood that these embodiments are merely illustrative of the principles and application of the present invention. It is therefore to be understood that numerous modifications may be made in the illustrative embodiments and that other arrangements may be devised without departing from the spirit and scope of the present invention as defined by the appended claims.

We claim:

1. An apparatus for casting an electrophoretic separation medium within a received tray having open ends, said apparatus comprising a housing, first sealing means and second sealing means arranged spaced apart within said housing for sealing the open ends of said tray when brought into engagement therewith, said first sealing means supporting a first gasket for sealing one open end of said tray and arranged opposing said second sealing means, said second sealing means supporting a second gasket and arranged opposing said first gasket for sealing the other open end of said tray, said first sealing means being movable with respect to said second sealing means, and guide means in operative association with said first sealing means for adjusting the spaced apart relationship between said first sealing means and said second sealing means so as to receive said tray therebetween with said open ends in sealing engagement with said first gasket and said second gasket.

2. The apparatus of claim 1 wherein said first sealing means comprises a first partition having said first gasket supported thereon.

3. The apparatus of claim 2 wherein said second sealing means comprises a second partition having said second gasket supported thereon, and said second partition movable relative to said first partition.

4. The apparatus of claim 2 wherein said second sealing means is supported by a portion of said housing and arranged opposing said first sealing means.

5. The apparatus of claim 1 wherein said guide means comprises a pair of spaced apart rods extending through said housing between said first sealing means and said second sealing means.

6. The apparatus of claim 5 wherein said first sealing means includes a pair of spaced apart openings each receiving one of said rods for permitting movement of said first sealing means along said rods in spaced relationship with said second sealing means.

7. The apparatus of claim 1 further including securing means for maintaining said first sealing means and said second sealing means in engagement with said open ends of said tray.

8. An apparatus for casting an electrophoretic separation medium within a received first tray having open ends, said apparatus comprising a housing, first sealing means and second sealing means arranged opposing one another in spaced apart relationship within said housing for sealing the open ends of said tray when brought into engagement therewith, said first sealing means and said second sealing means being movable with respect to each other, guide means in operative association with said first sealing means and said second sealing means for adjusting the spaced apart relationship between said sealing means to provide a first opening for receiving said tray with its open ends in engagement with said first sealing means and said second sealing means, and a bar removaby arranged between and in engagement with a portion of said housing and said first sealing means for maintaining said first sealing means and said second sealing means in sealing engagement with said open ends of said tray while casting said separation medium therein, said first tray being removable from said apparatus upon removal of said bar from its engaged position.

9. The apparatus of claim 8 wherein said first sealing means and said second sealing means each comprise a partition having a gasket arranged opposing one another for sealing the open ends of said tray when within said first opening.

10. The apparatus of claim 9 wherein said guide means comprises a pair of spaced apart rods extending through said housing between said first sealing means and said second sealing means.

11. The apparatus of claim 10 wherein said partitions formed of said first sealing means and said second sealing means are movably supported by said rods for movement of said partitions in spaced relationship with one another to provide said first opening having a variable size.

12. The apparatus of claim 8 wherein said spaced apart relationship of said first sealing means and said second sealing means further provides a second opening between a portion of said housing and said second sealing means for receiving therein a second tray having open ends.

13. The apparatus of claim 12 further including third sealing means supported by said housing within said second opening for sealing one open end of said second tray while its other open end is sealed by said second sealing means.

14. The apparatus of claim 13 wherein said second sealing means comprises a partition having a gasket arranged on both sides thereof and opposing said first sealing means and said third sealing means.

15. The apparatus of claim 14 wherein said bar arranged between said first sealing means and a portion of said housing maintains said first sealing means, second sealing means and third sealing means in engagement with the open ends of said first tray and said second tray provided within said first opening and said second opening.

16. An apparatus for casting an electrophoretic gel within a plurality of received trays having open ends, said apparatus comprising a housing, a first seal element, a second seal element, and a third seal element, said seal elements arranged within said housing in spaced apart relationship, said first seal element and said second seal element being movable with respect to each other, guide means for adjusting the relative position of said first seal element and said second seal element within said housing for providing (1) a first receiving portion between said first seal element and second seal element for receiving a first tray therein with its open ends in engagement with said first seal element and said second seal element and (2) a second receiving portion between said second seal element and said third seal element for receiving a second tray therein with its open ends in engagement with said second seal element and said third seal element, and securing means for maintaining said first seal element, said second seal element and said third seal element in sealing engagement with the open ends of said first tray and said second tray.

17. The apparatus of claim 16 wherein said first seal element comprises a first partition having a gasket on one side thereof, said second seal element comprises a second partition having a gasket on opposite sides thereof, one gasket of said second partition opposing said gasket of said first partition, and said third seal element comprising a gasket supported by a portion of said housing opposing the other gasket of said second partition.

18. The apparatus of claim 17 wherein said guide means comprises a pair of parallel spaced apart rods extending through said housing for movably supporting said first partition and said second partition thereon in spaced apart relationships for providing said first receiving portion and said second receiving portion.

19. The apparatus of claim 18 wherein said securing means comprises a removable rod arranged between a portion of said housing and said first partition.

20. The apparatus of claim 16 wherein said first tray and second tray are of different length.

* * * * *

UNITED STATES PATENT AND TRADEMARK OFFICE
CERTIFICATE OF CORRECTION

PATENT NO. : 4,618,408

DATED : October 21, 1986

INVENTOR(S) : Richard Malavarca, et al.

It is certified that error appears in the above-identified patent and that said Letters Patent is hereby corrected as shown below:

Column 4, line 25, after "rod" insert --insert 154-- (second occurence only).

Column 8, line 20, after "and" insert --said--.

Signed and Sealed this

Twenty-fourth Day of February, 1987

Attest:

DONALD J. QUIGG

Attesting Officer     Commissioner of Patents and Trademarks